United States Patent [19]

Miller et al.

[11] Patent Number: 5,346,142
[45] Date of Patent: Sep. 13, 1994

[54] CONTINUOUS SHREDDING APPARATUS FOR MEDICAL WASTE MATERIAL AND METHOD FOR USE THEREOF

[75] Inventors: Charles R. Miller, Houston; Haskell B. Berry, Jr., Channel View, both of Tex.

[73] Assignee: Premier Medical Technology Inc., Houston, Tex.

[21] Appl. No.: 14,877

[22] Filed: Feb. 5, 1993

[51] Int. Cl.⁵ .............................................. B02C 23/38
[52] U.S. Cl. ...................................... 241/21; 241/29; 241/152.2; 241/606; 241/DIG. 38
[58] Field of Search .............. 241/606, 154, 29, 101.8, 241/101.2, 21, 152.1, 152.2, DIG. 38

[56] References Cited

U.S. PATENT DOCUMENTS

| | | | |
|---|---|---|---|
| 1,321,380 | 11/1919 | Liggett | 241/152.21 |
| 1,459,713 | 6/1923 | Beggs | 241/152.2 X |
| 3,735,932 | 5/1973 | Bradley | 241/101.8 X |
| 4,344,579 | 8/1982 | Morita et al. | 241/154 X |
| 4,578,185 | 3/1986 | Wilson et al. | 241/606 X |
| 4,884,756 | 12/1989 | Pearson | 241/606 X |
| 4,964,914 | 10/1990 | Leath | 241/29 |
| 5,048,766 | 9/1991 | Gaylor et al. | 241/154 X |
| 5,054,696 | 10/1991 | Mennel et al. | 241/606 X |
| 5,227,137 | 7/1993 | Sadr | 251/DIG. 38 X |
| 5,236,135 | 8/1993 | Wilson et al. | 241/21 |

FOREIGN PATENT DOCUMENTS

| | | |
|---|---|---|
| 54823 | 6/1982 | European Pat. Off. .... 241/DIG. 38 |
| 1380979 | 11/1972 | United Kingdom . |
| 2124512 | 2/1984 | United Kingdom . |

Primary Examiner—Mark Rosenbaum
Assistant Examiner—Frances Han
Attorney, Agent, or Firm—Keck, Mahin & Cate

[57] ABSTRACT

A continuous method for shredding waste material, particularly medical waste material, includes continuously loading the waste material into a hopper; passing the waste material into a continuously running primary shredder; initially shredding the waste material in the primary shredder; passing the initially shredded material into a continuously conveying screw conveyor wherein the initially shredded material is mixed together; conveying the mixed material into a continuously running high speed shredder for further shredding; passing the further shredded material into a turbo blender for additionally reducing the particle size of the shredded material; removing the shredded material by conveyor to a discharging area, and discharging the shredded waste material to a receptacle. The apparatus used for shredding the waste material includes a closable hopper for receiving the waste material; a primary shredder for receiving waste material from the hopper which includes a plurality of blades for initially shredding the waste material; a screw conveyor for mixing the material before passing the material to a high speed shredder; a high speed shredder having cutting blades for shredding the mixed material which is then passed to a turbo blender for further mixing and breaking down the shredded, mixed material. The method includes sterilizing the waste, if needed, and sterilized, shredded waste material is discharged to a receptacle.

24 Claims, 1 Drawing Sheet

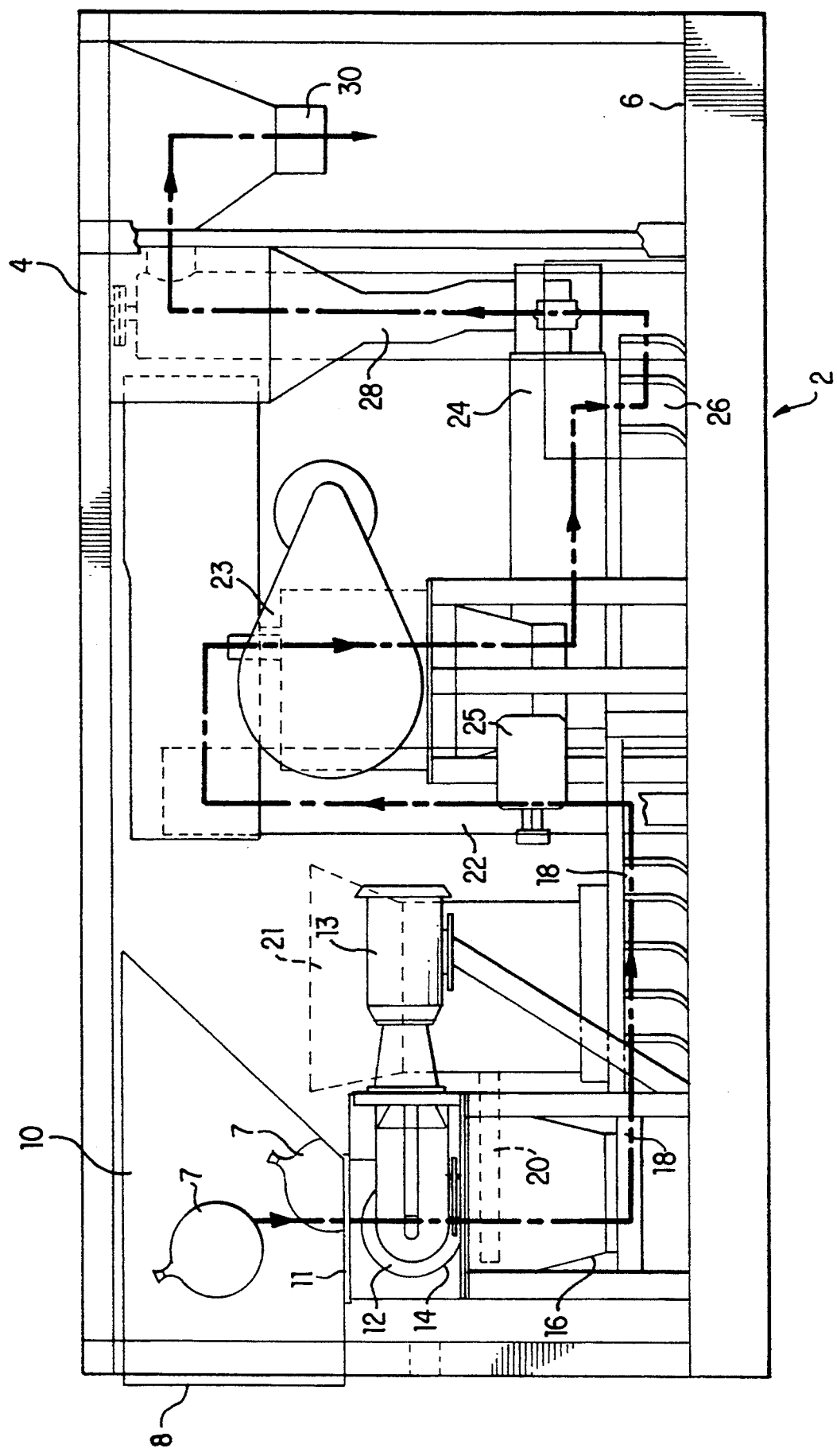

CONTINUOUS SHREDDING APPARATUS FOR MEDICAL WASTE MATERIAL AND METHOD FOR USE THEREOF

FIELD OF THE INVENTION

The invention relates to continuous shredding apparatus for waste material, preferably medical waste material, which can grind the waste material, to an unrecognizable state.

BACKGROUND OF THE INVENTION

Prior shredding apparatus for hospital waste material has not been operable continuously and has not been able to shred the waste to an unrecognizable state. Batch feed shredding apparatus is slow and cannot shred the large quantities of waste generated by a hospital to an unrecognizable state which allows efficient sterilization of the waste due to its shredded size. Leaving large pieces of unshredded material does not allow the shredded material to be efficiently sterilized.

SUMMARY OF THE INVENTION

A continuous method for shredding waste material, preferably medical waste material, includes continuously loading the waste material into a hopper; passing the waste material into a continuously running primary shredder; initially shredding the waste material in the primary shredder; passing the initially shredded material into a continuously conveying screw conveyor wherein the initially shredded material is mixed together; conveying the mixed material into a continuously running high speed shredder for further shredding; passing the further shredded material into a turbo blender for additionally reducing the particle size of the shredded material; removing the shredded material by conveyor to a discharging area, and discharging the shredded waste material to a receptacle. The apparatus used for shredding the waste material includes a closable hopper for receiving the waste material; a primary shredder for receiving waste material from the hopper which includes a plurality of blades for initially shredding the waste material; a screw conveyor for mixing the material before passing the material to a high speed shredder; a high speed shredder having cutting blades for shredding the mixed material which is then passed to a turbo blender for further mixing and breaking down the shredded, mixed material. The sterilized, shredded waste material is discharged to a receptacle.

The apparatus is particularly advantageous in that the product is finely shredded, intimately mixed, and thoroughly disinfected and sterilized to remove all infectious pathogens.

It is an object of the invention to provide a continuous shredding apparatus for waste material, particularly for hospital waste material, which shreds the material until the original material is substantially unrecognizable in the shredded product.

It is another object of the invention to provide a method for continuously shredding waste material, particularly hospital waste material, which produces a sterilized product in which the original material is substantially unrecognizable in the discharged product.

BRIEF DESCRIPTION OF THE DRAWING

The Figure is a schematic elevational view of apparatus of the invention.

DETAILED DESCRIPTION OF THE PREFERRED EMBODIMENTS

The apparatus described is used for a continuous method in which waste material, in particular hospital waste, is loaded in plastic bags into the apparatus, shredded into unrecognizable state, preferably treated with sterilant and greatly reduced in quantity for disposal. The apparatus can shred any hospital waste, including hospital sharps, into unrecognizable form. The material leaving the apparatus is in suitable form for disposal. The apparatus can also be used as a batch feed apparatus if small amounts of material only need to be shredded. Continuous operation for large amounts of material is economical and preferred.

The waste material may include many kinds of waste material. In a typical use, hospital waste of all kinds, including syringes and needles, surgical tools, paper goods, textiles, plastics, glass, surgical waste including body parts or any other hospital waste material which may be sterile or non-sterile is shredded. Hospitals have very large amounts of waste material which must be carefully disposed of and the apparatus and method described herein is particularly suitable for disposing of hospital waste which must be thoroughly disinfected or sterilized before disposal to destroy infectious pathogens. The agent used for sanitation to sterilize, disinfect and destroy infectious pathogens is described herein as a "sterilant". For other types of waste material, a sterilant may not be needed. The apparatus is highly efficient so that the waste is shredded and mixed to a fine state where the material appears homogeneous and the types of materials disposed of, even needles and sharps, are completely unrecognizable.

The apparatus may be operated automatically after it has been turned on. Jamming is unusual, but safety features are provided. If a shredder jams, it can be reversed to free the jam, and then the process is continued.

After initiating activation of the apparatus, untreated, unsterilized waste material, which is usually contained in bags, is loaded through a loading door at the side or top of the apparatus into a hopper. The bags may be loaded continuously from a conveyor or loaded by hand. Unbagged material may also be loaded.

The apparatus used is described with reference to the accompanying drawing. The Figure is a schematic view of apparatus 2 used for shredding waste material, particularly hospital waste. The frame 4 of the apparatus may be a steel structure having a steel plate welded to the bottom thereof to form a floor 6 onto which the component structures are mounted. Apparatus 2 is supplied with sources of water and electricity. The apparatus is preferably enclosed in a sheet metal casing (not shown) and is soundproofed using known sound-deadening material.

The waste material may include any hospital waste, syringes and needles, surgical tools, paper goods, textiles, plastics, glass or any other waste material from any other source which may be sterile or non-sterile. In a typical example, the apparatus is loaded with "red bags" of hospital waste which may need to be disinfected or sterilized before disposal in landfill or otherwise. Waste treated using the apparatus and method of using the apparatus described herein meets standards set forth by government agencies.

Bags 7, such as "red bags" of hospital waste, or bags of other waste material, are loaded through side loading door 8, or top loading door 9, into loading hopper 10, for starting the shredding procedure. The door may be a sliding door or other suitable door known in the art. The waste material passes through an open entry 11 into primary shredder 12. Primary shredder 12 includes a pair of shafts having a plurality of parallel disc cutters along the length of each shaft. The discs may, in a non-limiting example, be 12 in. diameter discs, about 1 in. in thickness. The discs of the two shafts intermesh with each other for shredding the waste material therebetween. The primary shredder is powered by a 10 hp, 1200 rpm electric motor 13 which is geared down to allow the two shafts to rotate at 40 rpm and 60 rpm. When the shafts rotate at different speeds, the shredding efficiency is improved and jamming of the shredder is avoided. A shredder of this type is manufactured by Franklin Miller, Livingston, N.J. 07039.

A screen 14, which may be a 1.5 inch mesh screen is disposed below the intermeshing discs of the shredder, spaced from the discs and following the outer contours thereof. Typically, the screen may be spaced with close tolerance to the cutting edges of the discs of the primary shredder. As the waste material circulates through the primary shredder, the material small enough to pass through the screen falls through a chamber 16 to a horizontal conveyor 18.

As the waste material falls through chamber 16, it may be sprayed from spray arm 20, or otherwise mixed, with a sterilant, stored in hopper 21. Sterilant may additionally or alternatively be added to the waste material before it enters the primary shredder or while it is being shredded in the primary shredder, or as otherwise known in the art. Either the sterilant is liquid or liquid, typically water, is added to enable thorough mixing of the shredded material in the conveyor.

Horizontal conveyor 18 includes a screw conveyor powered by a ½ hp motor, turning at 150 rpm. The conveyor is lined with a sleeve made of lubricious, slippery plastic material. The lubricious material is non-absorbent, hard and relatively frictionless. Similar material is used to cover the screw flight edges. As the screw of the conveyor travels along the sleeve, the edges of the screw wipe the surface of the lining sleeve of the conveyor, moving forward all the material in the conveyor and thoroughly mixing it as it is conveyed. After being thoroughly mixed, the material passes into a vertical conveyor 22, for further conveying and mixing, and for elevation to a height sufficient for entering high speed shredder 23.

Vertical conveyor 22 is also a screw conveyor which further mixes the initially shredded material as it is conveyed. The vertical conveyor 22 is powered by a 3 hp motor and runs at 225 rpm. Particularly intimate mixing may occur at the junction of the horizontal conveyor 18 and the vertical conveyor 22. If preferred, a slanting conveyor may be used to elevate the initially shredded and mixed material, in place of the horizontal and vertical conveyors.

The conveyed, mixed waste material then enters the high speed shredder 23. High speed shredder 23 is, in a non-limiting example, a single shaft disc cutter powered by a 15 hp motor (not shown) at 1725 rpm. The shaft of the high speed disc cutter rotates at about 450 rpm. The discs preferably have carbide tips. In the high speed shredder 23, the initially shredded material is further shredded, and then passes to a turbo blender 24 which is powered by a 10 hp motor 25 operating at 1725 rpm. The shaft of the turbo blender 24 turns at 1400 rpm, in the non-limiting example described herein. The turbo blender 24 includes a cylinder which is, for example, 12 ins. in diameter and 4 ft. long. A 2 in. shaft carries a plurality of paddles having carbide tips. A turbo blender of the type used is made by Scott Equipment Company, New Prague, Minn. 56071. Any substantially sized pieces of material remaining after the shredding are shattered as well as being mixed, while in the turbo blender 24. Thus, even if the waste material entering the system includes, for example, many needles, after passing through the turbo blender 24, the needles are shattered into tiny pieces.

From the turbo blender 24, the waste material passes by horizontal conveyor 26 and vertical conveyor 28 conveyor to a discharge outlet 30, where the material may be bagged, boxed or conveyed away in any known manner. The conveyor, shown as horizontal conveyor 26 and vertical conveyor 28 may be a combination horizontal/vertical conveyor, as described, or other conveyor known in the art.

In a preferred embodiment of the apparatus, an automatically controlled hopper 21 for sterilant is provided and the sterilant is injected into the primary shredder 12 or into the hopper 16 below the primary shredder 12 to allow the shredded waste material to be mixed with sterilant as it is conveyed to the high speed shredder 23. Sterilant may be added at other positions in the apparatus in a similar way, as appropriate, so that the product discharged from the apparatus is sterile.

The product discharged for removal from the system is a sterile product if sterilant is used. While the invention is particularly suitable for processing hospital waste, such as liquids, surgical waste including body tissues and bone, textiles, plastics, glass up to about 5 in. in diameter, metal including syringe needles, surgical tools, etc., wooden items, including tongue depressors, etc, paper, tiles and other waste materials to produce a sterile product, it will be appreciated that this is a non-limiting example, and uses for other types of sterile and non-sterile waste will be apparent to those skilled in the art. The shredded waste material is substantially dry, particulate and greatly reduced in volume at the end of the cycle.

The method of using the apparatus 2 is indicated by the broken line schematic flow line shown in the Figure. The waste material is fed through the primary shredder and guided into the screw conveyor for thorough mixing, shown here as a horizontal conveyor followed by a vertical conveyor. The shredded, mixed waste then passes into the high speed shredder, and after further shredding enters the turbo blender for mixing and shattering. The waste leaving the blender is conveyed to the discharge outlet.

The combination of the primary shredder, having shafts preferably rotating at different speeds and the conveyor in which the shredded material is integrally mixed before further shredding in the high speed shredder ensures a completely mixed, finely shredded product. Further mixing and comminuting to small particles in the turbo blender ensures an intimately mixed, finely shredded product. The turbo blender may not be needed for all applications, but its use is preferred, particularly where a sterile product is required.

In a typical apparatus according to the invention, the machine is encased in a sheet metal casing and may be about 7 ft. in height, 5 ft. wide and 14 ft. long. Depending on the amount and type of material fed to the apparatus, the residence time of the waste material in the apparatus may be between about 1 minute and about 10 minutes, generally about 2 to 6 minutes.

While the invention has been described with respect to certain embodiments thereof, variations and modifications may be made without departing from the spirit and scope of the invention.

We claim:

1. A method for shredding medical waste material comprising:
   loading waste material into a hopper;
   passing the waste material into a primary shredder;
   initially shredding the waste material in the primary shredder;
   adding sterilant to the initially shredded waste material;
   passing the initially shredded material into a first continuously conveying screw conveyor wherein the initially shredded material and sterilant are mixed together;
   conveying the mixed material into a high speed shredder rotating at a higher speed than said primary shredder;
   further shredding the mixed material in the high speed shredder;
   removing the shredded material by a second conveyor to a discharging area, and
   discharging the sterilized shredded waste material.

2. A method according to claim 1 wherein the primary shredder comprises disc cutters mounted on a pair of shafts wherein said disc cutters intermesh with each other, and the method comprises shredding the waste material between the intermeshed disc cutters.

3. A method according to claim 2 wherein a screen is disposed below the primary shredder, and the method comprises shredding the waste material sufficiently for the waste material to pass through said screen.

4. A method according to claim 2 comprising rotating the shafts of the disc cutters at different speeds from each other.

5. A method according to claim 1 comprising mixing shredded waste material with sterilant after said material has been shredded in the primary shredder.

6. A method according to claim 1 comprising adding liquid to the shredded waste material before mixing in the screw conveyor.

7. A method according to claim 6 comprising passing the initially shredded material into a horizontal screw conveyor.

8. A method according to claim 7 comprising subsequently passing the material into a vertical screw conveyor for further mixing.

9. A method according to claim 1, wherein residence time of the waste material in the apparatus is between about 1 minute and about 10 minutes.

10. A method according to claim 9, wherein residence time is about 2 to 6 minutes.

11. A method according to claim 1, wherein the primary shredder is a dual shaft disc cutter and the high speed shredder is a single shaft disc cutter.

12. A method for continuously shredding and sterilizing medical waste material comprising:
   loading medical waste material into a hopper;
   passing the medical waste material into a primary shredder;
   initially shredding the medical waste material in the primary shredder;
   adding sterilant to the initially shredded medical waste material;
   passing the initially shredded material into a continuously conveying screw conveyor wherein the initially shredded material and sterilant are thoroughly mixed together;
   conveying the mixed shredded hospital waste material into a high speed shredder rotating at a higher speed than the rotation speed of the primary shredder for further shredding;
   conveying and mixing the further shredded material in a screw conveyor for further mixing;
   removing the shredded, mixed material which is substantially sterile and which is shredded sufficiently that no recognizable waste material remains, by conveyor to a discharging area, and
   discharging the shredded medical waste material.

13. A method according to claim 12, wherein the step of passing the initially shredded material into a continuously conveying screw conveyor comprises passing the material into conveying means having an inlet end at a lower level than an outlet end thereof whereby the material being conveyed moves upwardly during mixing thereof.

14. A method according to claim 12, wherein the step of passing the initially shredded material into a continuously conveying screw conveyor comprises passing the material into conveying means which is slanted diagonally upward.

15. Apparatus for shredding medical waste material comprising:
   a closable hopper for receiving waste material;
   a primary shredder for receiving waste material from the hopper, said shredder comprising a plurality of blades for initially shredding the waste material;
   means for adding sterilant to the waste material;
   means for passing the initially shredded material to means for conveying the material to a high speed shredder; wherein said conveying means comprises screw conveyor means for mixing the initially shredded material together forming mixed, initially shredded material;
   a shredder having high speed cutting blades for rotating at a higher speed than the speed of rotation of the blades of the primary shredder for further shredding the mixed, initially shredded material; and
   means for discharging the sterilized, shredded waste material to a receptacle.

16. Apparatus according to claim 15 wherein said first conveying means for mixing the shredded material comprises at least one screw conveyor.

17. Apparatus according to claim 16 wherein said first conveying means comprises a substantially horizontal screw conveyor followed by a vertical screw conveyor.

18. Apparatus according to claim 15 wherein said first screw conveyor is lined with a sleeve of lubricious material.

19. Apparatus according to claim 15, wherein the primary shredder is a dual shaft disc cutter and the high speed shredder is a single shaft disc cutter.

20. Apparatus for shredding and sterilizing medial waste material comprising;
   a closable hopper for receiving medical waste material;
   a primary shredder for receiving the waste material from the hopper, said chamber comprising a plurality of blades for initially shredding the waste material;

means for adding sterilant to the medical waste material;

first means for thoroughly mixing said sterilant with said shredded medical waste material and conveying the shredded material mixed with sterilant, wherein said first mixing and conveying means comprises screw means for mixing and conveying the initially shredded material and said sterilant together;

a shredder having high speed cutting blades for receiving the material from said first mixing and conveying means and finely shredding the mixed, initially shredded material;

second mixing and conveying means for further mixing the finely shredded material and sterilant; and means for discharging the sterilized, shredded waste material to a receptacle.

21. Apparatus according to claim 20, wherein the second mixing and conveying means comprises an inlet end at a lower level than the outlet end whereby the material being mixed is conveyed upwardly during mixing.

22. Apparatus according to claim 20, wherein the first mixing and conveying means comprises an inlet end at a lower level than the outlet end whereby the material being mixed is conveyed upwardly during mixing.

23. Apparatus according to claim 22 wherein the first mixing and conveying means comprises an upwardly slanting screw conveyor.

24. Apparatus according to claim 22 wherein the second mixing and conveying means comprises an upwardly slanting screw conveyor.

* * * * *